United States Patent
Hubert et al.

(10) Patent No.: US 11,389,056 B2
(45) Date of Patent: Jul. 19, 2022

(54) EYE ASSESSMENT DEVICES AND METHODS TO ASSESS EYESIGHT

(71) Applicant: Essilor International, Charenton-le-Pont (FR)

(72) Inventors: Julien Hubert, Charenton-le-Pont (FR); Bruno Fermigier, Charenton-le-Pont (FR); Aude Bouchier, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 224 days.

(21) Appl. No.: 16/342,519

(22) PCT Filed: Oct. 16, 2017

(86) PCT No.: PCT/EP2017/076376
§ 371 (c)(1),
(2) Date: Apr. 16, 2019

(87) PCT Pub. No.: WO2018/073187
PCT Pub. Date: Apr. 26, 2018

(65) Prior Publication Data
US 2019/0246892 A1    Aug. 15, 2019

(30) Foreign Application Priority Data
Oct. 20, 2016  (EP) ..................................... 16194932

(51) Int. Cl.
*A61B 3/032*    (2006.01)
*A61B 3/00*    (2006.01)
(Continued)

(52) U.S. Cl.
CPC ............ *A61B 3/032* (2013.01); *A61B 3/0008* (2013.01); *A61B 3/036* (2013.01); *A61B 3/066* (2013.01); *A61B 3/0041* (2013.01); *G03H 1/0005* (2013.01)

(58) Field of Classification Search
CPC ....... A61B 3/032; A61B 3/0008; A61B 3/036; A61B 3/066; A61B 3/0041; A61B 3/005; A61B 3/0058; G03H 1/0005
(Continued)

(56) References Cited

U.S. PATENT DOCUMENTS 7,339,711 B2    3/2008  Kuroda et al.
9,895,057 B2    2/2018  Tumlinson
(Continued)

FOREIGN PATENT DOCUMENTS

CN          1653394 A    8/2005
CN        102314894 A    1/2012
(Continued)

OTHER PUBLICATIONS

International Search report, dated Nov. 13, 2017, from corresponding PCT Application No. PCT/EP2017/076376.
Office Action issued in Chinese Patent Application No. 201780064721.0 dated Mar. 3, 2021.
Office Action issued in Chinese Patent Application No. 201780064721.0 dated Apr. 13, 2022.

*Primary Examiner* — Marin Pichler
(74) *Attorney, Agent, or Firm* — Nixon & Vanderhye (57) ABSTRACT

Disclosed are assessment devices and methods to assess eyesight. In one embodiment, an eyesight assessment device includes a medium having one or more imaging functionalities and operable to project images for display based on the one or more imaging functionalities. The device also includes an optical source operable to project light and being positioned at one or more positions relative to the medium, such that at least one of images are projected from the medium based on the position of the optical source relative (Continued)

to the medium and the one or more imaging functionalities of the medium, where each image corresponds to an object provided for display at a virtual distance relative to a user of the eyesight assessment device, and where each image includes one or more of user assessable display characteristics that are indicative of a visual condition of the user.

16 Claims, 8 Drawing Sheets

(51) Int. Cl.
*A61B 3/036* (2006.01)
*A61B 3/06* (2006.01)
*G03H 1/00* (2006.01)

(58) Field of Classification Search
USPC .................................. 351/237, 223, 239–244
See application file for complete search history.

(56) References Cited

U.S. PATENT DOCUMENTS

| | | | |
|---|---|---|---|
| 10,736,501 B2* | 8/2020 | Breuninger | G02B 5/32 |
| 2005/0052715 A1 | 3/2005 | Avudainayagam et al. | |
| 2005/0259304 A1 | 11/2005 | Someno | |
| 2005/0275916 A1 | 12/2005 | Mitsuya | |
| 2012/0002257 A1 | 1/2012 | Shirakura et al. | |
| 2013/0201446 A1 | 8/2013 | Hall et al. | |
| 2016/0262608 A1* | 9/2016 | Krueger | G06T 19/006 |

FOREIGN PATENT DOCUMENTS

| | | |
|---|---|---|
| EP | 1 501 403 A1 | 2/2005 |
| WO | 03/090612 A1 | 11/2003 |
| WO | 2011/144939 A2 | 11/2011 |
| WO | 2015/162098 A1 | 10/2015 |

* cited by examiner

EYE ASSESSMENT DEVICES AND METHODS TO ASSESS EYESIGHT

FIELD OF THE INVENTION

The present disclosure relates generally to eye assessment devices and methods to assess eyesight.

BACKGROUND OF THE INVENTION

Approximately 4.5 billion individuals around the world suffer from one or more forms of visual conditions that require some form of vision correction. Examples of visual conditions include, but are not limited to myopia, hyperopia, astigmatism, and color blindness. Unfortunately, only approximately 1.9 billion individuals out of the 4.5 billion individuals that suffer from at least one form of visual condition adequately correct their eyesight. Approximately 95% of the 2.6 billion individuals that live with uncorrected vision live in developing countries where they lack awareness of the impact of poor vision and access to basic vision care.

An eye chart having several lines of characters is often utilized to perform visual acuity tests that measure the sharpness of a patient's vision. More particularly, the patient often stands approximately 5 meters or at another required distance from the eye chart and attempts to read the smallest line of characters at the required distance. However, the required distance between the patient and the eye chart may not be observed by the patient, which would result in inaccurate visual acuity tests. Further, the foregoing types of visual acuity tests may only assess certain types of visual conditions such as myopia, but may not adequately assess other types of visual conditions, such as hyperopia. As such, there is a need for a device and a method to accurately determine variously visual conditions of the patient.

One object of the present invention is to provide accurate eye assessment devices and methods to accurately assess eyesight.

SUMMARY OF THE DISCLOSED EMBODIMENTS

The disclosed embodiments provide eyesight assessment devices and methods to assess eyesight. In accordance with one embodiment, an eyesight assessment device includes a medium having one or more imaging functionalities and operable to project one or more images for display based on the one or more imaging functionalities. The eyesight assessment device also includes an optical source operable to project light and being positioned at one or more positions relative to the medium, such that at least one of the one or more images are projected from the medium based on the position of the optical source relative to the medium and the one or more imaging functionalities of the medium, where each image of the one or more images corresponds to an object provided for display at a virtual distance relative to a user of the eyesight assessment device, and where each image of the one or more images includes one or more of user assessable display characteristics that are indicative of a visual condition of the user.

In accordance with another illustrative embodiment, a method to assess eyesight is provided. The method includes positioning a medium having one or more imaging functionalities proximate to a user, the medium being operable to project one or more images for display based on the one or more imaging functionalities, each image of the one or more images corresponding to an object provided for display at a virtual distance relative to the user, and each image of the one or more images having a one or more user assessable display characteristics indicative of a visual condition of the user. The method also includes positioning an optical source at a first position of one or more positions relative to the medium. The method further includes transmitting light from the optical source towards the medium to project a first image of the one or more images from the first position. The method further includes obtaining a first user assessment of one or more user assessable display characteristics of the first image. The method further includes determining the visual condition of the user based on the first user assessment.

In accordance with a further illustrative embodiment, another eye assessment device is provided. The eye assessment device includes a holographic medium having one or more imaging functionalities and operable to project one or more images for display based on the one or more imaging functionalities, where each image of the one or more images corresponds to an object provided for display at a virtual distance relative to user, and where each image of the one or more images comprises one or more user assessable display characteristics that are indicative of a visual condition of the user. The eye assessment device also includes a housing for storing the holographic medium, the housing having at least one position for positioning an optical source at one or more positions relative to the holographic medium, the optical source being operable to project light toward the holographic medium to project at least one image of the one or more images based on the position of the optical source relative to the holographic medium. The housing also contains an aperture configured for the user of the eyesight assessment device to observe the one or more images through said aperture.

Additional details of the disclosed embodiments are provided below in the detailed description and corresponding drawings.

BRIEF DESCRIPTION OF THE DRAWINGS

Illustrative embodiments of the present invention are described in detail below with reference to the attached drawing Figures, which are incorporated by reference herein, and wherein.

The illustrated figures are only exemplary and are not intended to assert or imply any limitation with regard to the environment, architecture, design, or process in which different embodiments may be implemented.

DETAILED DESCRIPTION

Figure 1:
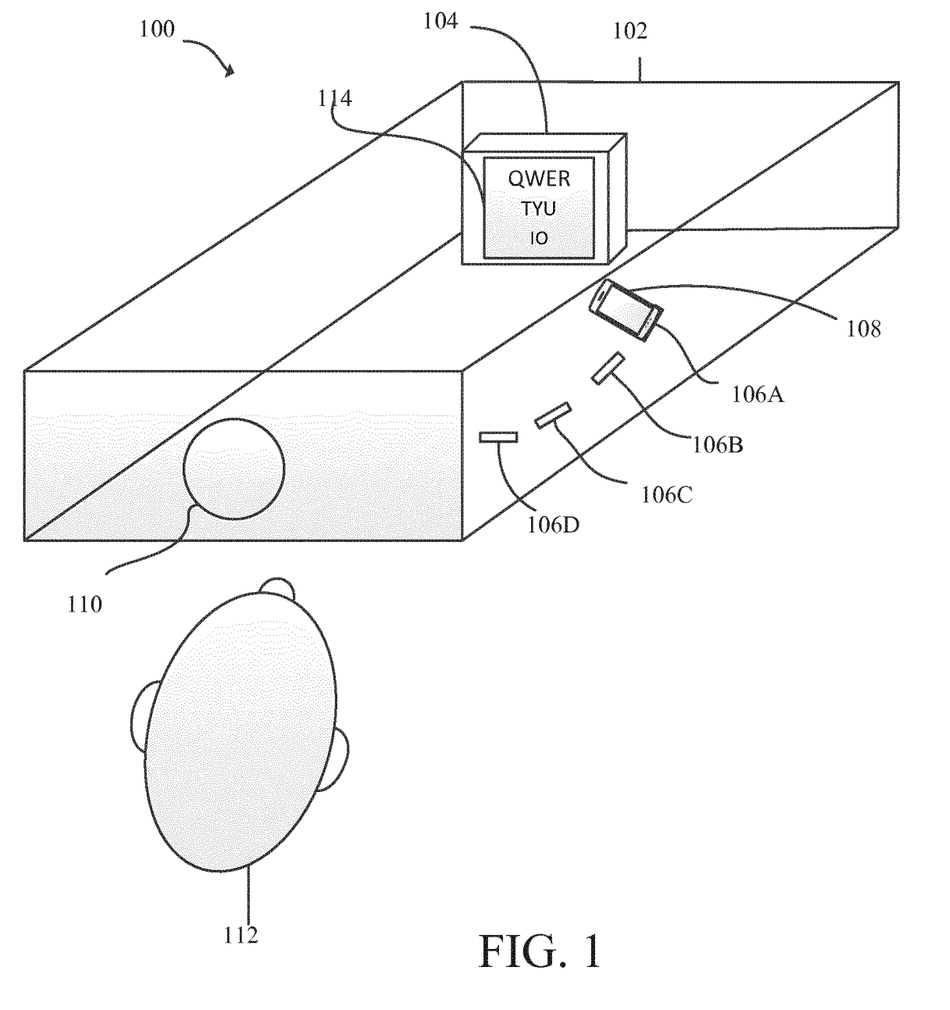
FIG. 1 is a schematic view of an eyesight assessment device having an optical source and a medium having imaging functionalities operable to provide images for display at a virtual distance relative to a user of the eyesight assessment device.

FIG. 1 is a schematic view of an eyesight assessment device 100 having an optical source 108 and a medium 104 having imaging functionalities operable to provide images for display at a virtual distance relative to a user 112 of the eyesight assessment device 100. The eyesight assessment device 100 includes a housing 102 that partially or completely encapsulates the optical source 108 and the medium 104. The eyesight assessment device 100 also includes position indicators 106A-106D indicative of one of four positions that the optical source 108 may be positioned at relative to the medium 104 to provide images, such as first image 114 for display at a virtual distance from the user 112, where the virtual distance represents a user perceived distance between an image such as the first image 114, and the user 112. The eyesight assessment device 100 further includes an aperture 110, through which the user 112 may view an object that defines the first image 114, where the object represents an eyechart, as well as other images that are provided for display at one or more virtual distances relative to the user 112.

The optical source 108 includes any electronic device and/or optoelectronic device operable to project light. In some embodiments, the optical source 108 is a flash component of a smartphone, tablet computer, personal digital assistance (PDA), laptop computer, laser source, and/or the flash component of another electronic device or optoelectronic device operable to project light. In the embodiment of FIG. 1, the optical source 108 is a flash component of a smartphone. In other embodiments, the optical source 108 is a display screen of one of the foregoing electronic or optoelectronic devices, where light is projected from the display screen of the respective electronic or optoelectronic device. In one of such embodiments, the optical source is a display screen of a smartphone, and images, such as the first image 114 are projected by the display screen of the smartphone towards the medium 104.

The medium 104 represents any type of medium having one or more imaging functionalities and are operable to provide images such as the first image 114 for display at one or more virtual distances from the user 112. As defined herein, an imaging functionality is a function of the medium 104 that generates images for display. In some embodiments, the medium 104 is a holographic film, and the imaging functionality of the holographic film records one or more holographic images on the holographic film, and generates the holographic images when light from the optical source 108 is projected on the holographic film. In other embodiments, the medium 104 is a set of diffraction lenses, and the imaging functionality of the diffractive lenses is operable to reflect and refract images projected by the optical source 108 at one or more different reflective and refractive powers, respectively. In further embodiments, the medium 104 is a set of mirrors having one or more refractive and/or reflective powers, and the imaging functionality of the set of mirrors is operable to modify display sizes of images projected by the optical source 108 based on one or more refractive and/or reflective powers of the set of mirrors. In one of such embodiments, the set of mirrors is a set of holographic mirrors recorded by one or more holographic methods in a holographic film. Additional examples of the medium 104 and one or more imaging functionalities of the medium 104 are described herein and are illustrated in at least FIGS. 2-7.

First position indicator 106A represents a first position that the optical source 108 may be positioned at relative to the medium 104 to provide images for display. As illustrated in FIG. 1, the first image 114 is provided for display at a first virtual distance relative to the user 112 when the optical source 108 is positioned at the first position 106A. The first image 114 corresponds to the eyechart having three lines of letters, where the font of each line of letters has a different font size. Further, the first image 114 is displayed at the first virtual distance relative to the user 112. The user 112 may identify one or more letters of the eyechart and an assessment of the visual condition of the user 112 may be made based on the accuracy of the user 112. As such, the different sizes of the letters of the eyechart may be utilized as a user assessable display characteristic that is indicative of a visual condition of the user 112, such as whether the user 112 is suffering from myopia, and the degree of myopia. In addition to varying the font size of different lines of letters, letters on different lines may also be provided for display in different colors to assess whether the user 112 suffers from color blindness. For example, the top line of the eyechart may be provided for display in red, the middle line of the eyechart may be provided for display in blue, and the bottom line of the eyechart may be provided for display in green. The user 112, in addition to identifying the content of each line of the eyechart, may also identify the color of the content of each line of the eyechart.

Second, third, and fourth position indicators 106B-106D represent additional positions that the optical source 108 may be positioned at relative to the medium 104 to provide images for display. In some embodiments, the first image is provided for display at different virtual distances relative to the user 112 when the optical source 108 is positioned at the second, third, and fourth position indicators 106B, 106C, and 106D, respectively. For example, when the optical source 108 is positioned at the first position indicator 106A, content of the eyechart is displayed at a virtual distance of 5 meters relative to the user 112, such that the user 112 perceives the content of the eyechart as if a physical copy of the eyechart is displayed at a distance of 5 meters from the user 112. Further, when the optical source 108 is positioned at the second, third, and fourth position indicators 106B, 106C, and 106D, the user 112 perceives the content of the eyechart as if the eyechart is displayed at a distance of 4 meters, 3 meters, and 1 meter, respectively. Given that the virtual distances correspond to physical distances as perceived by the user 112, the first image 114 of the eyechart may be displayed at a virtual distance and the eyechart may be assessed by the user 112 as if a physical copy of the eyechart is actually displayed at a corresponding physical distance. As such, the eye assessment device 100 eliminates inaccuracies associated with placing a physical copy of the eyechart an incorrect physical distance from the user 112.

In some embodiments, the eye assessment device 100 includes one or more positioning guides that ensure the optical source 108 is approximately positioned at one of the four position indicators 106A-106D to ensure the accuracy of the eye assessment device 100. In one of such embodiments, an imaging functionality of the medium 104 projects an error message if the optical source 108 is not positioned correctly relative to the medium 104. In further embodiments, variations of the first image 114 are provided for display when the optical source 108 projects light towards the medium 104 while positioned at the second, third, and fourth position indicators 106B, 106C, and 106D. For example, the content of the eyechart, the color of one or more lines of the eyechart, the size of the eyechart, the orientation of the eyechart, the clarity of the eyechart, the contrast of the eyechart, as well as the virtual distance of the eyechart may be varied when the optical source 108 is positioned at different position indicators 106A-106D. Therefore, an assessment of one or more of the user's visual conditions, such as myopia, hyperopia, astigmatism, as well as other types of visual conditions may be made by varying the position of the optical source 108 relative to the medium 104.

In some embodiments, the housing 102 includes one or more slots or inserts (not shown) that aligns the optical source 108 with the first, second, third and fourth position indicators 106A-106D. In other embodiments, the housing 102 includes other manual or automatic positioning mechanisms to position the optical source 108 at the first, second, third, and fourth position indicators 106A-106D. In some embodiments, the housing 102 includes user instructions that indicate how to properly position the optical source 108 along one of the four position indicators 106A-106D. In further embodiments, when the optical source 108 is positioned at one or more of the first, second, third, or fourth position indicators 106A-106D, multiple images are provided for display at different virtual distances relative to the user 112.

Although FIG. 1 illustrates four position indicators 106A-106D positioned in front of the medium 104, the optical source 108 may be positioned at a different number of positions in front of or behind the medium 104. Further, although the first image 114 appears to be provided for display at approximately the same position as the medium 104, in some embodiments, the first image 114 may also appear in front of the medium 104 or behind the medium 104. As defined herein, the user 112 is always positioned in front of the medium 104 and faces a front side of the medium 104. As such, the optical source 108 is positioned front of the medium 104 if the optical source 108 and the user 112 both face an identical side of the medium 104, whereas the optical source 108 is positioned behind the medium 104 if the optical source 108 and the user 112 face different sides of the medium 104. Additional descriptions of positioning the optical source 108 relative to the medium 104, and obtaining one or more images are provided in the following paragraphs and are illustrated in at least FIGS. 2-7.

Figure 2:
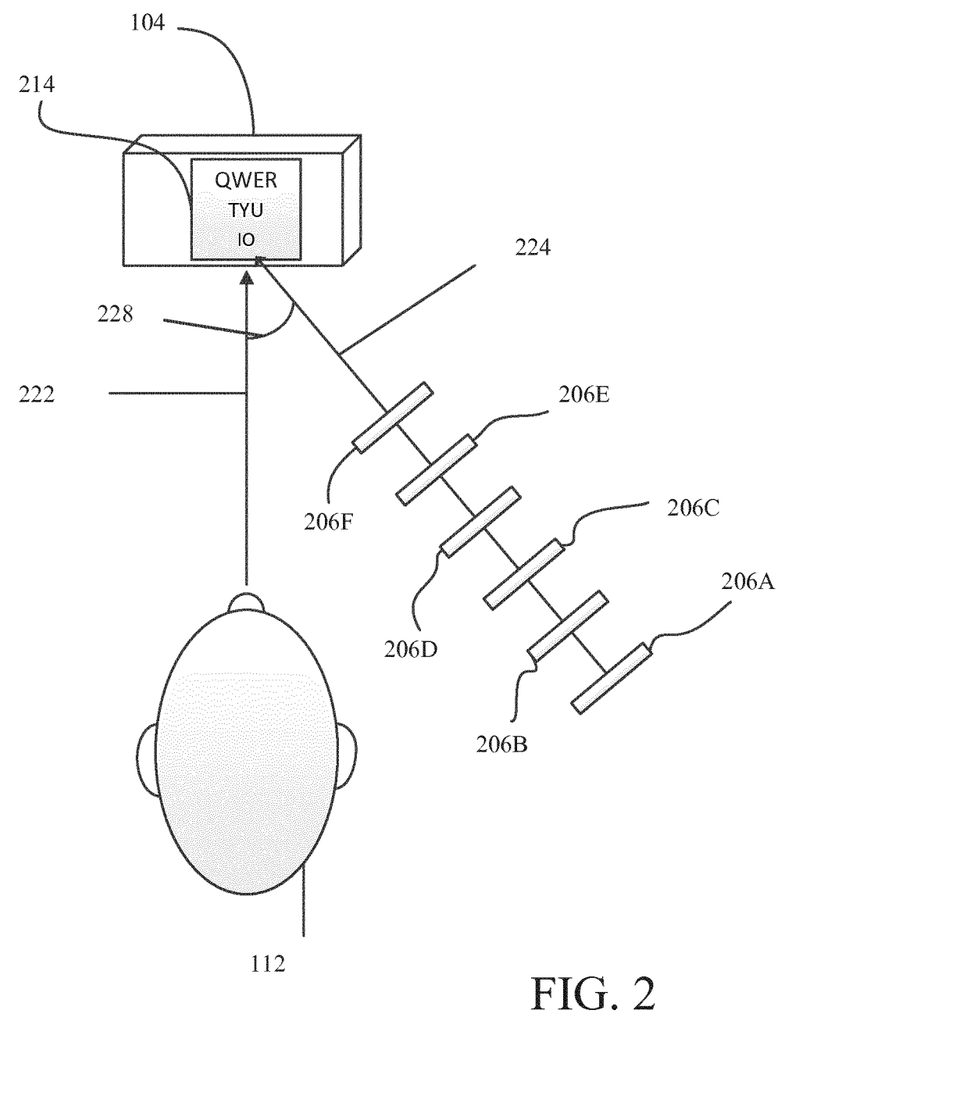
FIG. 2 is a schematic interior view of the eyesight assessment device of FIG. 1, where the optical source may be positioned at multiple positions relative to the medium to project an eyechart for display at different virtual distances from the user.

FIG. 2 is a schematic interior view of the eyesight assessment device 100 of FIG. 1, where the optical source 108 may be positioned at multiple positions relative to the medium 104 to project an eyechart for display at different virtual distances from the user 112. In the embodiment of FIG. 2, first, second, third, fourth, fifth, and sixth position indicators 206A-206F represent different locations the optical source 108 may be positioned at relative to the medium 104 to project the eyechart. In the embodiment of FIG. 2, the optical source 108 is positioned at the first position indicator 206A and projects light traveling along a direction indicated by arrow 224 towards the medium 104. The medium 104 is a holographic film having a first holographic image 214 of an eyechart having content in red (red colored eyechart) recorded on the holographic film, and is operable to project the recorded first holographic image 214 for display at a virtual distance of 0.3 meters from the user 112 when light from the optical source 108 positioned at the first position indicator 206A is projected onto the holographic film.

Further, holographic images of eyecharts similar to the eyechart of the first holographic image 214 are also recorded on the holographic film and are provided for display when the optical source 108 is positioned at the second, third, fourth, fifth, and sixth position indicators 206B-206F. For example, a second holographic image of a turquoise colored eyechart is recorded on the holographic film and is provided for display at a virtual distance of 0.5 meters from the user 112 when light from the optical source 108 positioned at the second position indicator 206B is projected onto the holographic film. Further, a third holographic image of a purple colored eyechart is recorded on the holographic film and is provided for display at a virtual distance of 1 meter from the user 112 when light from the optical source 108 positioned at the third position indicator 206C is projected onto the holographic film. Further, a fourth holographic image of a yellow colored eyechart is recorded on the holographic film and is provided for display at a virtual distance of 2 meters from the user 112 when light from the optical source 108 positioned at the fourth position indicator 206D is projected onto the holographic film. Further, a fifth holographic image of a blue colored eyechart is recorded on the holographic film and is provided for display at a virtual distance of 3 meters from the user 112 when light from the optical source 108 positioned at the fifth position indicator 206E is projected onto the holographic film. Further, a sixth holographic image of a green colored eyechart is recorded on the holographic film and is provided for display at a virtual distance of 5 meters from the user 112 when light from the optical source 108 positioned at the sixth position indicator 206F is projected onto the holographic film. In some embodiments, the physical distance between the optical source 108 and the medium 104 is between 10 centimeters and 50 centimeters.

In some embodiments, in addition to displaying different colored eyecharts at different virtual distances, additional user assessable characteristics of the eyecharts, such as the font of the eyecharts, the content of the eyecharts, the display size of the eyecharts, the display contrast of the eyecharts, the display clarity of the eyecharts, the orientation of the eyecharts, as well as other quantifiable characteristics may also be varied. In such embodiments, the user's assessment of these characteristics may be utilized to assess and to determine one or more visual conditions of the user 112. In some embodiments, each position indicator 206A-206F corresponds to a diopter of a corrective lens operable to correct a visual condition of the user 112. For example, the first position indicator 206A is a first physical distance from the medium 104 and corresponds to a first diopter of a first corrective lens. The first corrective lens may be utilized to correct the visual condition of the user 112 if the user 112 is unable to identify one or more user assessable display characteristics, such as correctly identical all of the letters in the middle line of the first holographic image 214 while the optical source 108 is positioned at the first position indicator 206A. Alternatively, if the user 112 is able to read the content of the first holographic image 214 while the optical source 108 is positioned at the first position indicator 206A, then the optical source 108 may be moved to the second position indicator 206B, which is a second physical distance from the medium and corresponds to a second diopter of a second corrective lens. As such, a corrective lens operable to correct the visual condition of the user 112 may be identified by moving the optical source 108 to one of the position indicators 206A-206F.

FIG. 2 illustrates six different positions indicators 206A-206F along which the optical source 108 projects light in the direction indicated by arrow 224, and at an approximately identical lighting angle represented by arc 228. As defined herein, a lighting angle is an angle of the light projected by the optical source 108 relative to a viewing direction of the user 112, which is indicated by arrow 222. The optical source 108 may also be positioned at different lateral distances relative to the user 112, and having different lighting angles. As defined herein, different lateral locations represent different locations along a plane that is substantially normal to a viewing direction of the user 112. In some embodiments, the optical source 108 may be positioned such that the lighting angle of the optical source 108 is between 45° and 85°. In one of such embodiments, a holographic image of a green eyechart is recorded on the holographic film and is provided for display at a virtual distance of 5 meters from the user 112 when light from the optical source 108 positioned at a position indicator having a lighting angle of approximately 50° is projected onto the holographic film. In another one of such embodiments, a holographic image of a blue eyechart is recorded on the holographic film and is provided for display at a virtual distance of 1 meter from the user 112 when light from the optical source 108 positioned at a position indicator having a lighting angle of approximately 80° is projected onto the holographic film. Although the foregoing paragraphs describe the medium 104 as a holographic film, the medium 104 may also represent a diffraction film, one or more types of optical lens such as a holographic optical lens, or a diffractive optical lens, or one or more types mirror such as a holographic mirror, or a diffractive mirror. In that regard, the imaging functionalities of the diffraction film, the optical lens, and/or the mirror are also operable to provide one or more images for display when light originating from the image source 108 is transmitted towards the diffraction film, the optical lens and/or the mirror.

Figure 3A:
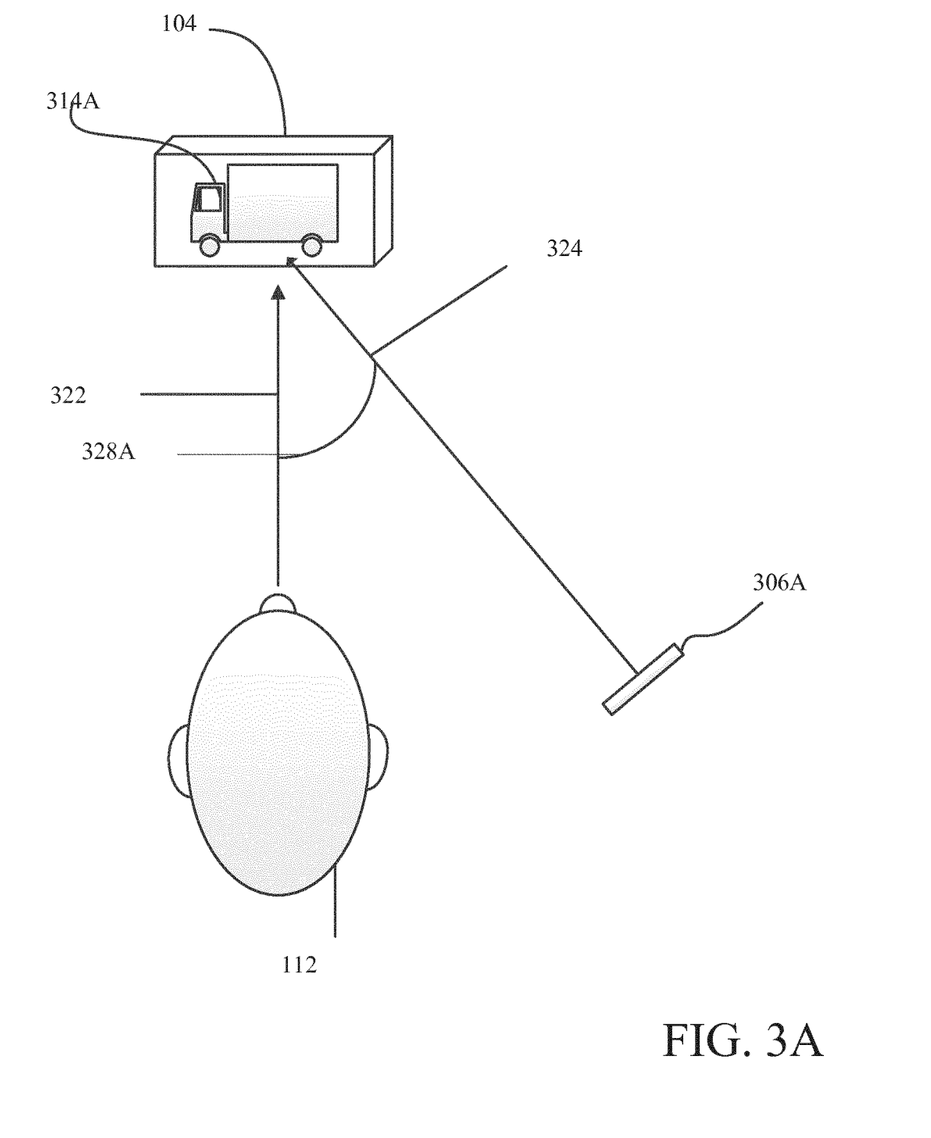
FIG. 3A is a schematic view of an eyesight assessment device, where the optical source is positioned at a first position relative to the medium to project a first image of a truck for display at a virtual distance from the user.
Figure 3B:
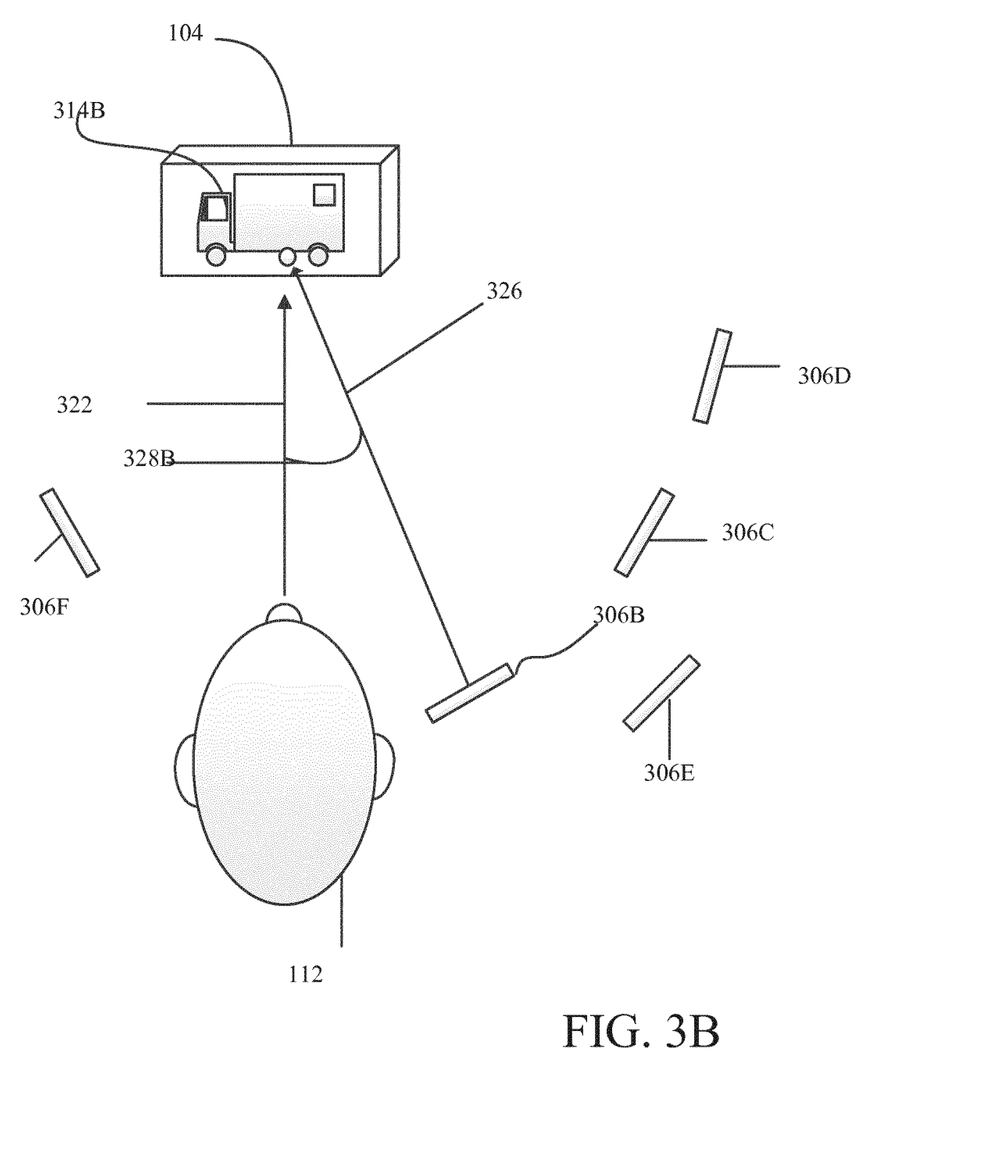
FIG. 3B is a schematic view of the eyesight assessment device of FIG. 3A, where the optical source is positioned at a second position relative to the medium to project a second image of a truck for display at the virtual distance from the user.

FIG. 3A is a schematic view of an eyesight assessment device, where the optical source 108 is positioned at a first position indicator 306A relative to the medium 104 to project a first image 314A of a truck for display at a virtual distance from the user 112. Light projected by the optical source 108 travels in a direction indicated by arrow 324. The viewing direction of the user 112 is represented by arrow 322. Light is projected towards the medium 104 at a first lighting angle represented by arc 328A. The imaging functionality of the medium 104 generates the first image 314A of a truck having two sets of wheels for display. FIG. 3B is a schematic view of the eyesight assessment device of FIG. 3A, where the optical source 108 is positioned at a second position indicator 306B relative to the medium 104 to project a second image 314B of a truck similar to the truck of the first image 314A for display at the virtual distance from the user 112. In the embodiment of FIG. 3B, light projected by the optical source 108 travels in a direction indicated by arrow 326. The viewing direction of the user 112 is represented by arrow 322. Light is projected towards the medium 104 at a second lighting angle represented by arc 328B. The imaging functionality of the medium 104 generates the second image 314B of a truck having three sets of wheels and a rear window for display. The slight variation of the trucks of the two images 314A and 314B provides two user assessable display characteristics that the user 112 may identify while viewing the two images 314A and 314B.

In some embodiments, in addition to the foregoing differences between the two images 314A and 314B, the virtual distances of the trucks, the display size of the trucks, the display contrast of the trucks, the display clarity of the trucks, the orientation of the trucks, as well as other quantifiable user assessable characteristics may also vary to assess the visual condition of the user 112. In some embodiments, the imaging functionality of the medium 104 is operable to provide additional images of trucks having slightly different user assessable display characteristics for display when the optical source 104 is positioned at third, fourth, fifth, and sixth position indicators 306C-306E. The variations of the images of the trucks may be assessed by the user 112 to determine the visual condition of the user 112.

Figure 4:
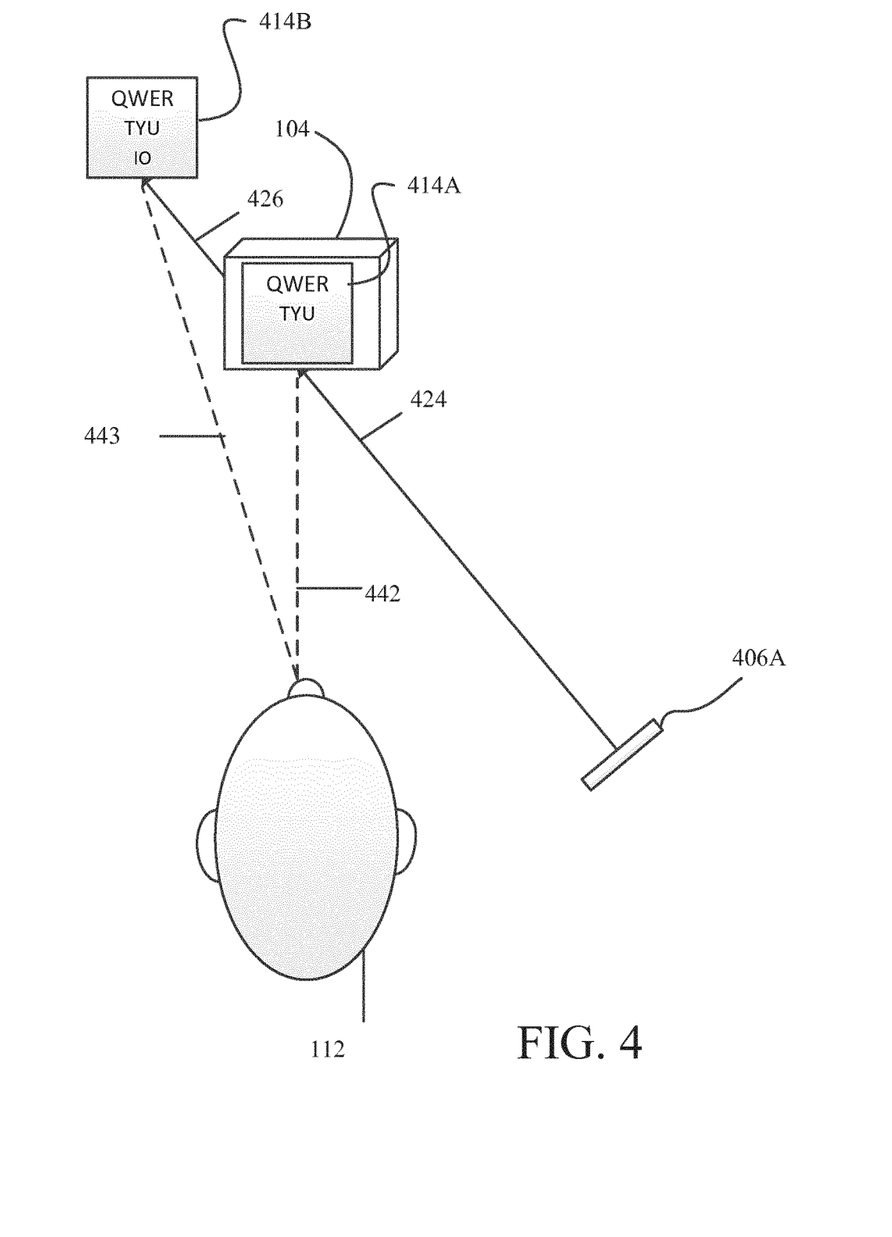
FIG. 4 is a schematic view of an eyesight assessment device, where two images are provided for display at two different virtual distances from the user.

FIG. 4 is a schematic view of an eyesight assessment device, where two images 414A and 414B are simultaneously provided for display at two different virtual distances from the user 112. The optical source 108 is positioned at a first physical indicator 406A and projects light in a direction indicated by arrows 424 and 426. The functionality of the medium 104 is operable to simultaneously project a first image 414A of an eyechart at a first virtual distance to the user 112 as indicated by first dash line 442 and a second image 414B of a second eyechart at a second virtual distance to the user 112 as indicated by second dash line 443, where the second virtual distance is greater than the first virtual distance. The content of the second eyechart includes both lines of the first eyechart and an additional third line having a smaller font size relative to the display font of the first two lines of both eyecharts. In some embodiments, each line of content displayed on each eyechart corresponds to a diopter of a corrective lens. For example, if the user 112 is unable to correctively identify the bottom line of the second eyechart but is able to identify all other lines on both eyecharts, then the visual condition of the user 112 may be corrected by a first corrective lens having a first diopter. Further, if the user 112 is unable to correctly identify the bottom and middle lines of the second eyechart but is able to identify all other lines of both eyecharts, then the visual condition of the user 112 may be corrected by a second corrective lens having a second diopter. Further, if the user 112 is only able to correctly identify the top line of the first eyechart, then the visual condition of the user 112 may be corrected by a third corrective lens having a third diopter.

The first and second eyecharts may contain additional user assessable characteristics that are different from each other. For example, the display contrast, the display clarity, the display color, as well as other user assessable characteristics discussed herein may also vary to assess the visual condition of the user 112. Although FIG. 4 illustrates two images 414A and 414B, the imaging functionality of the medium 104 may simultaneously provide additional numbers of images for display at different virtual distances relative to the user 112.

Figure 5:
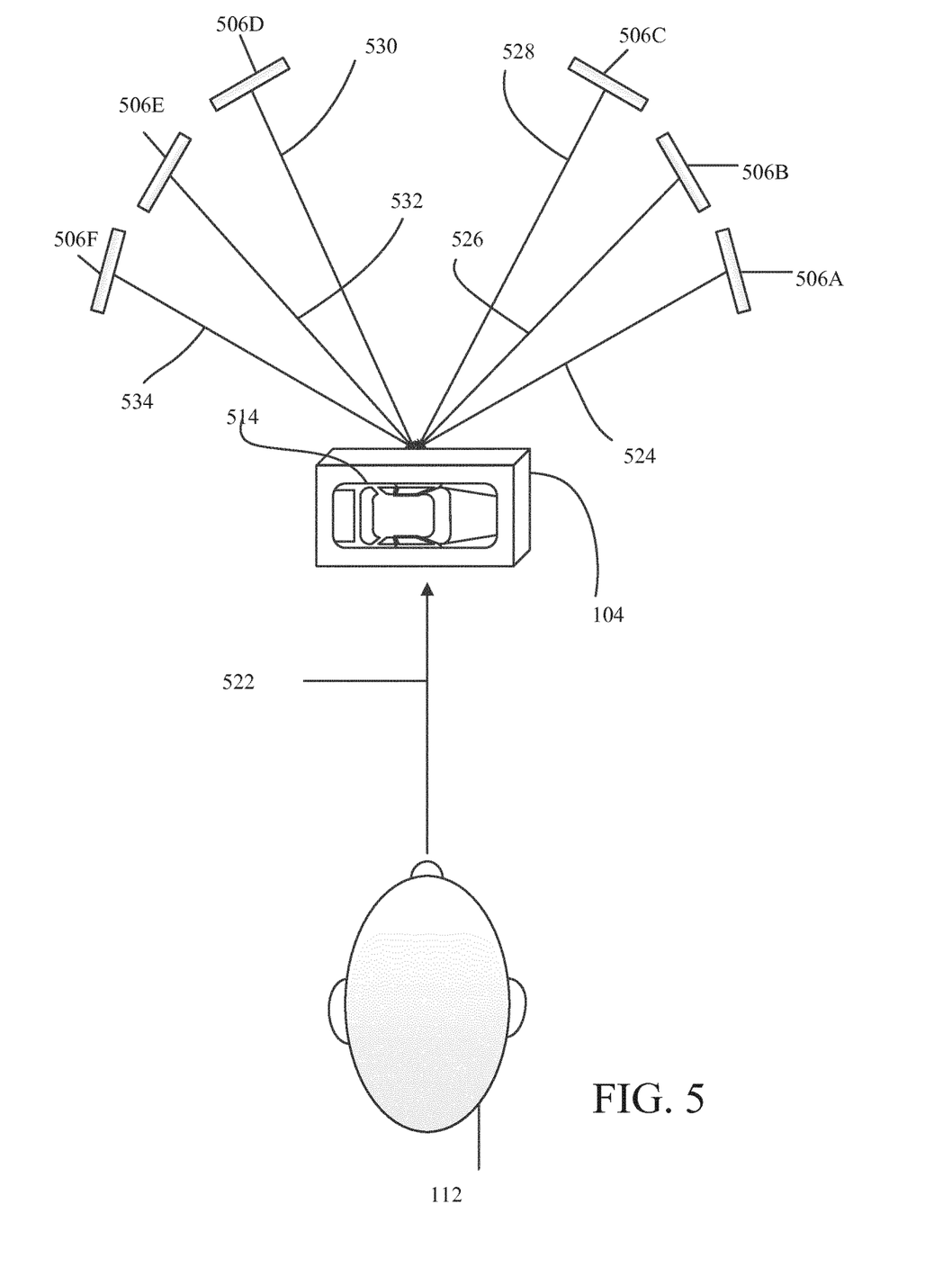
FIG. 5 is a schematic view of an eyesight assessment device, where the optical source may be positioned at multiple positions behind the medium to project an image of an automobile for display at a virtual distance from the user.

FIG. 5 is a schematic view of an eyesight assessment device, where the optical source 108 may be positioned at multiple positions 506A-506F behind the medium 104 to project an image, such as first image 514 of an automobile for display at a virtual distance from the user 112, when the user 112 is viewing the medium in a direction indicated by arrow 522. In the embodiment of FIG. 5, the first image 504 is a transmission image. As defined herein, a transmission image is an image generated by one or more imaging functionalities of the medium 104 when the user 112 is positioned in front of the medium 104 and when light from an optical source 108 positioned behind medium 104 is projected on the medium 104.

In the embodiment of FIG. 5, the first image 514 is projected when the optical source 108 is positioned at the first position indicator 506A and light projected by the optical source 108 travels toward the medium 104 in a direction indicated by first arrow 524. The imaging functionality of the medium 104 is further operable to project additional images of similar automobiles when the optical source 108 is positioned at second, third, fourth, fifth, and six position indicators 506B-506F and light projected by the optical source 108 travels toward the medium in directions indicative by second, third, fourth, fifth, and sixth arrows 526, 528, 530, 532, and 534, respectively. In some embodiments, one or more user assessable characteristics of the different automobiles, such as the color of the automobile, the display size of the license plate, the display color of the automobile, the number of doors on the automobile, as well as other user identifiable characteristics of the automobile may vary to assess one or more visual conditions of the user 112. In some embodiments, the imaging functionality of the medium 104 is operable to simultaneously project multiple transmission images for display. In such embodiments, the user 112 may assess one or more user assessable characteristics of the simultaneously projected images, and the visual condition of the user 112 may be determined based on the assessment of the one or more user assessable characteristics of the projected images.

Figure 6:
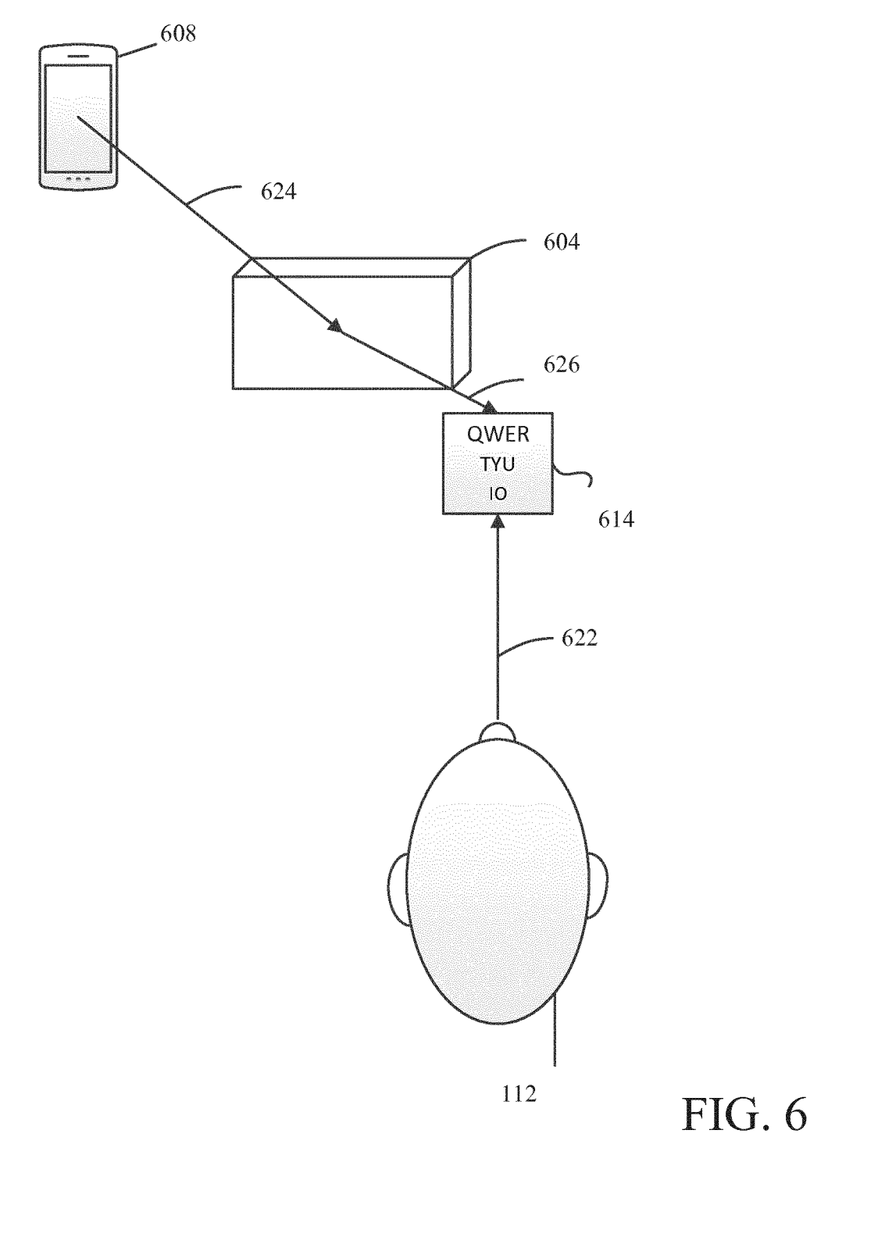
FIG. 6 is a schematic view of an eyesight assessment device, where a display screen of a smartphone projects an image of an eyechart towards a medium having one or more imaging functionalities operable to provide the image of the eyechart for display at a virtual distance from the user.

FIG. 6 is a schematic view of an eyesight assessment device, where a display screen of a smartphone 608 projects an image 614 of an eyechart towards a medium 604 having one or more imaging functionalities operable to provide the image 614 of the eyechart for display at a virtual distance from the user 112, where the user 112 is viewing the image 614 in a viewing direction indicated by arrow 622. The smartphone 608 is operable to generate one or more images such as the image 614 and is further operable to project the generated images from the display screen of the smartphone 608 towards the medium 604. In the embodiment of FIG. 6, the display screen of the smartphone 608 projects the image 614 in a direction indicated by arrow 624 towards the medium 604.

The imaging functionality of the medium 604 refracts the image 614 in a direction indicated by arrow 626, where the image 614 is provided for display at a virtual distance relative to the user 112. In some embodiments, the imaging functionality of the medium 604 provides a refractive power of the image 614. For example, if the smartphone 614 projects an image having a first dimension, the imaging functionality of the medium 604 is operable to augment the dimensions of the image based on the refractive power of the medium 604. In some embodiments, the refractive power of the medium 604 may be manually and/or dynamically adjusted to vary the display dimensions of one or more images projected by the display screen of the smartphone 608. Although the smartphone 608 is positioned behind the medium 604, the smartphone 608 may also be positioned in front of the medium 604 such that the display screen of the smartphone 608 faces the front side of the medium 604. In such embodiments, the imaging functionality of the medium 604 is operable to reflect one or more images projected by the display screen of the smartphone 608 at one or more virtual distances relative to the user 112. In one of such embodiments, the imaging functionality of the medium 604 provides a reflective power of the one or more images. In one of such embodiments, the reflective power of the medium 604 may also be manually and/or dynamically adjusted to vary the display dimensions of the one or more images projected by the display screen of the smartphone 608.

In some embodiments, the medium 604 is formed by one or more holographic mirrors having imaging functionalities disclosed herein that reflect and/or refract images projected by the display screen of the smartphone 608 and provide the reflected and/or refracted images for display at a virtual distance relative to the user 112. In one of such embodiments, one or more holographic techniques are utilized to record the one or more holographic mirrors in holographic film. In other embodiments, the medium 604 is formed by one or more lenses having imaging functionalities disclosed herein that reflect and/or refract images projected by the display screen of the smartphone 608 and provide the reflected and/or refracted images for display at a virtual distance relative to the user 112. In further embodiments, the medium 604 is formed by one or more holographic diffractive gratings having imaging functionalities disclosed herein that reflect and/or refract images projected by the display screen of the smartphone 608 and provide the reflected and/or refracted images for display at a virtual distance relative to the user 112. In some embodiments, the smartphone 608 is operable to project multiple images towards the medium 604, and the imaging functionality of the medium 604 is operable to refract and/or reflect each of the multiple images, and provide each of the multiple images for display at different virtual distances relative to the user 112.

Figure 7:
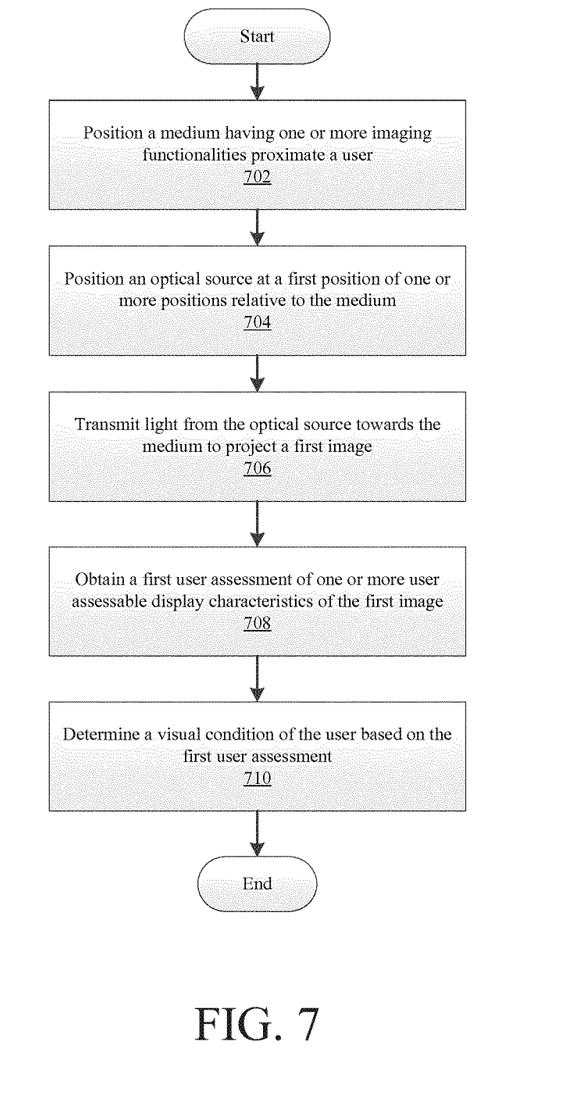
FIG. 7 is a flowchart illustrating a process to assess the user's eyesight.

FIG. 7 is a flowchart illustrating a process 700 to assess the user's eyesight. Although operations in the process 700 are shown in a particular sequence, certain operations may be performed in different sequences or at the same time where feasible. Further, although the following paragraphs describe utilizing the optical source 108 and the medium 104 to assess the user's eyesight, the process 700 may utilize other optical sources and mediums to determine the user's eyesight.

The process 700 starts when an image assessment device disclosed herein, such as the image assessment device 100 is provided to the user 112. At block 702, the medium 104 is positioned proximate to the user 112. As stated herein, the medium 104 has one or more imaging functionalities and that the medium 104 is operable to project one or more images for display based on the one or more imaging functionalities. In some embodiments, where the medium 104 is a holographic film, an imaging functionality of the holographic film records one or more holographic images on the holographic film, and generates the holographic images when light from the optical source 108 is projected on the holographic film. In other embodiments, the medium 104 is a set of diffraction lenses, and the imaging functionality of the diffractive lenses is operable to reflect and refract images projected by the optical source 108 at one or more different reflective and refractive powers, respectively. In further embodiments, the medium 104 is a set of holographic mirrors recorded in holographic film, and the imaging functionality of the set of mirrors is operable to modify display sizes of images projected by the optical source 108.

At block 704, the optical source 108 is positioned at a first position of one or more positions relative to the medium 104. The first position may be indicated by one of the various position indicators described herein and illustrated in FIGS. 1-6 or may be at another location relative to the medium 104. More particularly, the first position may be in front of the medium 104 or behind the medium 104. At block 706, light is transmitted from the optical source 108 towards the medium 104 to project a first image of the one or more images from the first position of the optical source 108. In some embodiments, where one or more images are pre-recoded on the medium 104, light projected by the optical source 108 projects the one or more images for display at one or more virtual distances from the user 112. In other embodiments, where light projected by the optical source 108 is indicative of one or more images projected by the optical source 108, the imaging functionality of the medium 104 is further operable to provide the projected one or more images for display at one or more virtual distances from the user 112. In one of such embodiments, the imaging functionality of the medium 104 is further operable to refract and/or reflect the projected one or more images at one or more different refractive and/or reflective powers.

Each of the one or more images that are provided for display is indicative of one or more objects disclosed herein, such as eyecharts, automobiles, as well as any other user perceivable objects. Further, each of the one or more images that are provided for display includes one or more user assessable display characteristics. For example, the virtual distance of the eyechart, the content of an eyechart, the display size of the content of the eyechart, the display contrast of the eyechart, the display clarity of the eyechart, the display color of the eyechart, the display orientation of the eyechart, as well as other user quantifiable display characteristics constitute as user assessable display characteristics that may be assessed by the user 112. At step 708, a first user assessment of the one or more user assessable display characteristics of the first image is obtained. Continuing with the previous example, the user assessment of the first image, where the first image is an eyechart may indicate which lines and letters the user 112 correctly identified, the color of the content of the eyechart, the orientation of the content of the eyechart, as well as the clarity and contrast of the content of the eyechart. At step 710, the visual condition of the user 112 is determined based on the first user assessment. Continuing with the previous example, if the eyechart is provided for display at a virtual distance of 5 meters from the user 112, and the user 112 has correctly identified only the top line of the eyechart, then the user 112 may be myopic and a lens having a first diopter may be operable to correct the visual condition of the user 112. Additional examples of determining the visual conditions of the user 112 based on the user assessment of user assessable characteristics are provided herein.

In some embodiments, the optical source 108 is repositioned at a second position indicator. Light is then transmitted from the optical source 108 while the optical source 108 is positioned at the second position indicator. In one of such embodiments, the imaging functionality of the optical source 108 is operable to project a second image corresponding to an object having common features and provided for display at a second virtual distance. Continuing with the previous example, the object of the second image may be a similar eyechart having identical content displayed at a further virtual distance than the virtual distance of the first image. A second user assessment of one or more user assessable display characteristics of the second eyechart, such as the display content of the second eyechart, the display color of the second eyechart, the display clarity of the second eyechart, as well as other display characteristics disclosed herein is obtained. The virtual condition of the user 112 is then determined based on the first user assessment of the first eyechart and the second user assessment of the second eyechart. Continuing with the previous example, if the first eyechart is provided for display at a virtual distance of 5 meters and the second eyechart is provided for display at a virtual distance of 30 centimeters and the user 112 is unable to identify any content on either eyecharts, then user 112 may be suffering from an astigmatism and a lens having a second diopter may be operable to correct the visual condition of the user 112.

The above disclosed embodiments have been presented for purposes of illustration and to enable one of ordinary skill in the art to practice the disclosed embodiments, but is not intended to be exhaustive or limited to the forms disclosed. Many insubstantial modifications and variations will be apparent to those of ordinary skill in the art without departing from the scope and spirit of the disclosure. For instance, although the flowcharts depict a serial process, some of the steps/blocks may be performed in parallel or out of sequence, or combined into a single step/block. The scope of the claims is intended to broadly cover the disclosed embodiments and any such modification. Further, the following clauses represent additional embodiments of the disclosure and should be considered within the scope of the disclosure:

Clause 1, an eyesight assessment device, comprising a medium having one or more imaging functionalities and operable to project one or more images for display based on the one or more imaging functionalities; and an optical source operable to project light and being positioned at one or more positions relative to the medium, such that at least one of the one or more images are projected from the medium based on the position of the optical source relative to the medium and the one or more imaging functionalities of the medium, wherein each image of the one or more images corresponds to an object provided for display at a virtual distance relative to a user of the eyesight assessment device, and wherein each image of the one or more images includes one or more of user assessable display characteristics that are indicative of a visual condition of the user.

Clause 2, the eyesight assessment device of clause 1, wherein the medium is at least one of a holographic and diffractive film, wherein the medium is formed from at least one of a holographic and diffractive film, wherein one of the one or more imaging functionalities of the holographic and diffractive film projects at least one of the one or more images, and wherein the optical source and the user are positioned to face an identical surface of the medium.

Clause 3, the eyesight assessment device of clause 1 or 2, wherein the one or more positions of the optical source correspond to different physical distances of the optical source relative to the at least one of the holographic and diffractive film, and wherein each physical distance is associated with an approximate diopter of a lens operable to correct the visual condition of the user.

Clause 4, the eyesight assessment device of at least one of clauses 1-3, wherein the one or more positions of the optical source correspond to different angles of the optical source relative to one of the at least one of the holographic and diffractive film, and wherein each angle is associated with an approximate diopter of a lens operable to correct the visual condition of the user.

Clause 5, the eyesight assessment device of at least one of clauses 1-4, wherein the medium is one of a holographic and diffractive film, wherein one of the one or more imaging functionalities projects transmission images, and wherein the optical source and the user are positioned to face different surfaces of the medium.

Clause 6, the eyesight assessment device of at least one of clauses 1-5, wherein the optical source is at least one of a flash component and a display screen of a smartphone, wherein the visual condition comprises at least one of myopia, hyperopia, astigmatism, and color blindness, and wherein one of the one or more the imaging functionalities projects an image recorded in the medium.

Clause 7, the eyesight assessment device of at least one of clauses 1-6, wherein the optical source is a display screen of an electronic device, the display screen being operable to project at least one of the one or more images, and wherein the one or more imaging functionalities comprises at least one of a first imaging functionality operable to refract the at least one images by a first refractive power and a second imaging functionality operable to reflect the at least one images by a first reflectively power.

Clause 8, the eyesight assessment device of at least one of clauses 1-7, wherein the one or more user assessable display characteristics comprises at least one of display color, display contrast, display size, and display clarity.

Clause 9, the eyesight assessment device of at least one of clauses 1-8, wherein the object is an eyechart, and wherein the one or more user assessable display characteristics comprises at least one of the display color of content of the eyechart, the display contrast of the content of the eyechart, the display size of the content of the eyechart, and the display clarity of the content of the eyechart.

Clause 10, the eyesight assessment device of at least one of clauses 1-9, wherein light transmitted by the optical source positioned at a first position of the one or more positions projects at least two images both corresponding to objects having common features and provided for display at different virtual distances relative to the user.

Clause 11, a method to assess eyesight, comprising positioning a medium having one or more imaging functionalities proximate to a user, the medium being operable to project one or more images for display based on the one or more imaging functionalities, each image of the one or more images corresponding to an object provided for display at a virtual distance relative to the user, and each image of the one or more images having a one or more user assessable display characteristics indicative of a visual condition of the user; positioning an optical source at a first position of one or more positions relative to the medium; transmitting light from the optical source towards the medium to project a first image of the one or more images from the first position; obtaining a first user assessment of one or more user assessable display characteristics of the first image; and determining the visual condition of the user based on the first user assessment.

Clause 12, the method of clause 11, further comprising repositioning the optical source to a second position of the one or more positions relative to the medium, transmitting light from the optical source towards the medium to project a second image of the one or more images from the second position, the first image and the second image corresponding to objects having common features provided for display at different virtual distances relative to the user; obtaining a second user assessment of one or more user assessable display characteristics of the second image; and determining the visual condition of the user based on the first user assessment and the second user assessment.

Clause 13, the method of clause 11 or 12, wherein the object is an eyechart, wherein the one or more user assessable display characteristics comprises at least one of a display color of the eyechart, a display contrast of the eyechart, a display size, and display clarity of the object, and wherein determining the visual condition of the user comprises comparing the first user assessment of at least one of the display color of content of the eyechart, the display contrast of the content of the eyechart, the display size of the content of the eyechart, and the display clarity of the content of the eyechart with the second user assessment of the display color, display contrast, display size, and display clarity of the object with the second user assessment of a corresponding user assessable display characteristic.

Clause 14, the method of at least one of clauses 11-13, wherein light from the optical source positioned at the first position projects the first image and a second image, the first image and the second image being one of holographic and virtual images and corresponding to objects having common characteristics and provided for display at different physical distances relative to the user and further comprising: obtaining a second user assessment of one or more user assessable display characteristics of the second image; and determining the visual condition of the user based on the first user assessment and the second user assessment.

Clause 15, an eyesight assessment device, comprising: a holographic medium having one or more imaging functionalities and operable to project one or more images for display based on the one or more imaging functionalities; a housing for storing the holographic medium, the housing comprising at least one position for positioning an optical source at one or more positions relative to the holographic medium, the optical source being operable to project light toward the holographic medium to project at least one image of the one or more images based on the position of the optical source relative to the holographic medium; and an aperture configured for a user of the eyesight assessment device to observe the one or more images through said aperture, wherein each image of the one or more images corresponds to an object provided for display at a virtual distance relative to the user, and wherein each image of the one or more images comprises one or more user assessable display characteristics that are indicative of a visual condition of the user.

As used herein, the singular forms "a", "an" and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

The invention claimed is:

1. An eyesight assessment device, comprising:
a medium having one or more imaging functionalities and operable to project a plurality of images for display based on the one or more imaging functionalities;
an optical source operable to project light; and
a plurality of position indicators including a first position indicator and a second position indicator,
wherein each image of the plurality of images corresponds to an object provided for display at a virtual distance relative to a user of the eyesight assessment device,
wherein each image of the plurality of images includes at least one user assessable display characteristic that is indicative of a visual condition of the user, the plurality of images including a first image and a second image, the first image including a first user assessable display characteristic of the at least one user assessable display characteristic, the second image including a second user assessable display characteristic of the at least one user assessable display characteristic different from the first user assessable display characteristic, and wherein the first image including the first user assessable display characteristic is projected from the medium when the optical source is positioned at the first position indicator and the second image including the second user assessable display characteristic is projected from the medium when the optical source is positioned at the second position indicator.

2. The eyesight assessment device of claim 1, wherein the medium is at least one of a holographic and diffractive film, wherein one of the one or more imaging functionalities of the holographic and diffractive film projects at least one of the plurality of images, and wherein the optical source and the user are positioned to face an identical surface of the medium.

3. The eyesight assessment device of claim 2, wherein the plurality of position indicators of the optical source correspond to different physical distances of the optical source relative to the at least one of the holographic and diffractive film, and wherein each of the physical distances is associated with an approximate diopter of a lens operable to correct the visual condition of the user.

4. The eyesight assessment device of claim 3, wherein the plurality of position indicators of the optical source correspond to different angles of the optical source relative to one of the at least one of the holographic and diffractive film, and wherein each angle is associated with an approximate diopter of a lens operable to correct the visual condition of the user.

5. The eyesight assessment device of claim 4, wherein the medium is one of a holographic and diffractive film, wherein one of the one or more imaging functionalities projects transmission images, and wherein the optical source and the user are positioned to face different surfaces of the medium.

6. The eyesight assessment device of claim 3, wherein the medium is one of a holographic and diffractive film, wherein one of the one or more imaging functionalities projects transmission images, and wherein the optical source and the user are positioned to face different surfaces of the medium.

7. The eyesight assessment device of claim 1, wherein the medium is one of a holographic and diffractive film, wherein one of the one or more imaging functionalities projects transmission images, and wherein the optical source and the user are positioned to face different surfaces of the medium.

8. The eyesight assessment device of claim 1, wherein the optical source is at least one of a flash component and a display screen of a smartphone, wherein the visual condition comprises at least one of myopia, hyperopia, astigmatism, and color blindness, and wherein one of the one or more imaging functionalities projects an image recorded in the medium.

9. The eyesight assessment device of claim 1, wherein the optical source is a display screen of an electronic device, the display screen being operable to project at least one image of the plurality of images, and wherein the one or more imaging functionalities comprises at least one of a first imaging functionality operable to refract the at least one image by a first refractive power and a second imaging functionality operable to reflect the at least one image by a first reflectively power.

10. The eyesight assessment device of claim 1, wherein the at least one user assessable display characteristic comprises at least one of display color, display contrast, display size, and display clarity.

11. The eyesight assessment device of claim 10, wherein the object is an eyechart, and wherein the at least one user assessable display characteristic comprises at least one of the display color of content of the eyechart, the display contrast of the content of the eyechart, the display size of the content of the eyechart, and the display clarity of the content of the eyechart.

12. The eyesight assessment device of claim 1, wherein the light transmitted by the optical source positioned at the first position indicator projects at least two images both corresponding to objects having common features and provided for display at different virtual distances relative to the user.

13. A method to assess eyesight with the eyesight assessment device according to claim 1, the method comprising:

positioning the medium having the one or more imaging functionalities proximate to a user, each image of the plurality of images corresponding to an object provided for display at a virtual distance relative to the user;

positioning the optical source at the first position indicator;

transmitting light from the optical source towards the medium to project the first image of the plurality of images from the first position indicator;

obtaining a first user assessment of the first user assessable display characteristic of the first image; and determining the visual condition of the user based on the first user assessment.

14. The method of claim 13, further comprising:

repositioning the optical source to the second position indicator;

transmitting light from the optical source towards the medium to project the second image of the plurality of images from the second position indicator, the first image and the second image corresponding to objects having common features provided for display at different virtual distances relative to the user;

obtaining a second user assessment of the second user assessable display characteristic of the second image; and determining the visual condition of the user based on the first user assessment and the second user assessment.

15. The method of claim 14, wherein the object is an eyechart, wherein the at least one user assessable display characteristic comprises at least one of a display color of the eyechart, a display contrast of the eyechart, a display size, and display clarity of the object, and wherein determining the visual condition of the user comprises comparing the first user assessment of at least one of the display color of content of the eyechart, the display contrast of the content of the eyechart, the display size of the content of the eyechart, and the display clarity of the content of the eyechart with the second user assessment of the display color, display contrast, display size, and display clarity of the object with the second user assessment of the second user assessable display characteristic.

16. The method of claim 13, wherein the first image and the second image are one of holographic and virtual images that correspond to objects having common characteristics and provided for display at different physical distances relative to the user, and the method further comprises:

obtaining the second user assessment of the second user assessable display characteristic of the second image; and determining the visual condition of the user based on the first user assessment and the second user assessment.

* * * * *